United States Patent [19]

Brunet et al.

[11] Patent Number: 4,801,093
[45] Date of Patent: Jan. 31, 1989

[54] PUSH-NIPPLE FOR MEDICAL SPRAYER

[75] Inventors: Michel Brunet, Colombe la Commanderie; Firmin Garcia, Evreux, both of France

[73] Assignee: Etablissements Valois, France

[21] Appl. No.: 623,867

[22] Filed: Jun. 25, 1984

[30] Foreign Application Priority Data

Jun. 24, 1983 [FR] France .............................. 83 10450

[51] Int. Cl.⁴ .............................................. B05B 1/34
[52] U.S. Cl. ....................................... 239/490; 239/493
[58] Field of Search ........... 222/402.1, 402.13, 402.15, 222/402.23, 402.25, 209, 211, 212, 215, 383; 239/490, 493, 497, 337; 604/37, 49, 54, 70, 73, 94, 183, 185, 146

[56] References Cited

U.S. PATENT DOCUMENTS

| 2,775,483 | 12/1956 | Treharne, Jr. et al. | 222/402.25 |
| 2,914,222 | 11/1959 | Meshberg | 222/402.13 X |
| 2,974,880 | 3/1961 | Stewart et al. | 239/493 |
| 3,129,893 | 4/1964 | Green | 239/490 |
| 3,169,673 | 2/1965 | Focht | 222/402.13 X |
| 3,323,690 | 6/1967 | Monahon | 222/402.13 |
| 3,363,808 | 1/1968 | Gorman | 222/215 X |
| 3,379,381 | 4/1968 | Decaux | 239/493 X |
| 3,406,911 | 10/1968 | Keeney | 239/490 |
| 3,493,179 | 2/1970 | Lee | 239/493 X |
| 3,635,406 | 1/1972 | Scheindel | 239/490 |
| 4,143,822 | 3/1979 | Bennett | 239/490 |
| 4,367,847 | 1/1983 | Bayer | 239/490 X |
| 4,371,097 | 2/1983 | O'Neill | 222/383 X |

Primary Examiner—Kevin P. Shaver
Attorney, Agent, or Firm—Sughrue, Mion, Zinn, Macpeak & Seas

[57] ABSTRACT

An elongate push-element (2) having a nozzle integrally formed with an external part (20) thereof, so that the nozzle cannot be forcibly ejected from a container which expels liquid under pressure. An opening (21a) at one end of an internal channel (21) may be slidably fitted on a valve stem (4) of a container (1), so that the push-element may be used with a variety of valve types.

3 Claims, 2 Drawing Sheets

PUSH-NIPPLE FOR MEDICAL SPRAYER

BACKGROUND OF THE INVENTION

The present invention relates to a push-nipple for medical sprayers, which spray medicines or other hygenic products into nostrils, ears, mouths, and other orifices. The invention is directed particularly to metering and non-metering sprayers fitted on a pressurized can, such as an aerosol can, as well as on manually-actuated pumps. More particularly, the present invention is directed to nozzles or sprayers which dispense a product in a whirling, or vortex fashion.

One-piece push-members, which can be mounted on a valve stem, are known. Vortex movement results from recesses and protrusions formed on the internal surface of the push-member and/or on the end of the valve stem. These prior art devices are disadvantageous because they are expensive to manufacture. Also, prior art nozzles have not been readily adaptable for use with any type of valve. An example of this prior art is French Patent No. 1,319,576.

Other more common devices have included a push-element which precisely engages a standard type valve stem. The push-element includes an internal channel as an extension of a central channel in the valve stem. The nozzle is housed in an enlarged recess at the other end of the internal channel. The nozzle is tightly held by being snugly fit, or by being attached in snap-on fashion by engagement of appropriate ridges on the nozzle and the internal channel. Such a system allows any push-element to be fitted on any type of valve stem; also, the system is less expensive to manufacture than the first one described.

The nozzle in the second type of system generally is held tightly, and is not pushed away from its housing during spraying, or by escape of fluid. However, there still is a danger of ejection of the nozzle. While nozzle ejection is not serious when perfume or even insecticide is being sprayed, there are situations where such a risk, however small, cannot be taken. For example, when a nozzle of an aerosol sprayer is to be inserted into a nostril to introduce nasal spray, or into the ear to introduce aural medicine, if the nozzle should be ejected, serious internal physical damage could result.

SUMMARY OF THE INVENTION

Accordingly, an object of the invention is to provide an aerosol sprayer push-element haveing an elongated shape to allow introduction into a physiological orifice. The inventive push-element has an internal channel of low cross-sectional area and a spraying chamber in front of an end opening of the internal channel. The nozzle of the push-element is molded along with the external part, and so is not separately inserted, but is integral with the external part, so that accidental ejection of the push-element is avoided.

An external part of the push-element has a central channel with one open end which fits onto a valve stem of a fluid container. The shape of this open end enables easy adjustability on the valve stem. The other end of the channel is mostly closed, but has an opening with a cross-sectional area smaller than that of the central channel. The opening also has at least one groove.

An internal part of the push-element comprises a rod which fits into the central channel of the external part, and has a smaller cross-sectional area than the central channel.

BRIEF DESCRIPTION OF THE DRAWINGS

The features and advantages of the present invention will become apparent from the following description when read in conjunction with the accompanying drawings, in which.

DETAILED DESCRIPTION OF A PREFERRED EMBODIMENT

Figure 1:
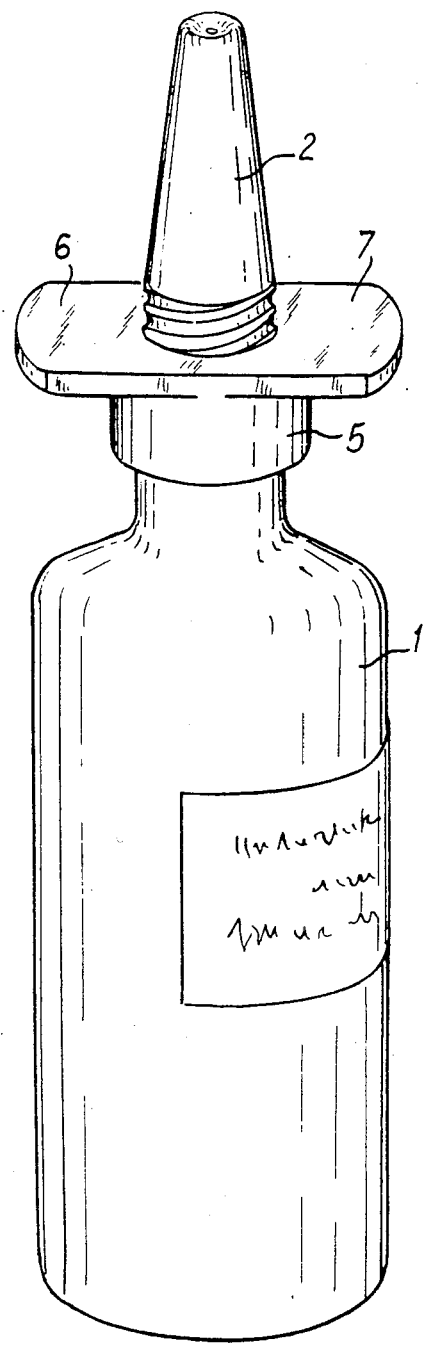
FIG. 1 is a perspective view of an aerosol bottle provided with a push-element according to the invention.

In FIG. 1, a bottle 1 has a push-element 2. The bottle may be made of a flexible material, expulsion of liquid under pressure being achieved by manually squeezing the bottle. Alternatively, the bottle may be made of a rigid material, expulsion of liquid under pressure being achieved under force of expulsion of a pressurized fluid which may or may not be mixed with the liquid to be applied. As yet another alternative, the spraying apparatus may comprise a hand-actuated pump.

A valve 3, which may be one of a variety of known types, includes a standard valve stem 4 on which any type of standard push-button may be fitted. The push-element 2 has an elongated tapered shape to permit insertion into a child's nostrils or ears, for example, to spray a medicine or other hygienic liquid. The push-element includes a skirt 5 for concealing the valve stem, and two flanges 6, 7 which allow the device to be well gripped or more easily actuated. A cap 8 can be snapped onto the push-element 2 to close it off from the air when the apparatus is not in use.

Figure 2:
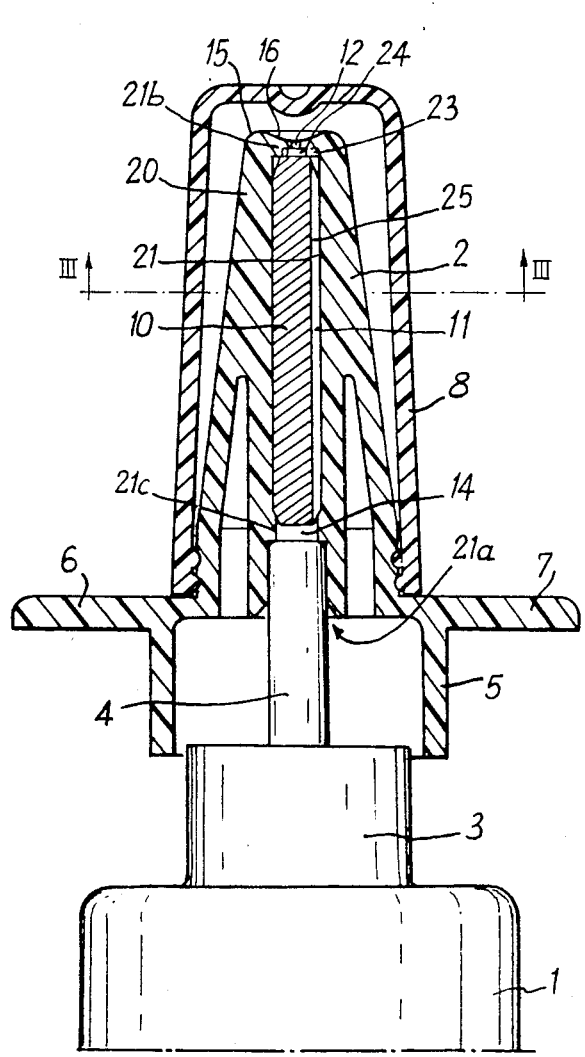
FIG. 2 is a cross-sectional view of the push-element in FIG. 1.

As shown in FIG. 2, the push-element includes an external part 20 which has a cylindrically-shaped central channel 21 which extends axially along the length of the external part 20. One end of the central channel has an opening 21a adapted to be slidably fitted onto valve stem 4. To facilitate this slidable fitting, channel 21 has a shoulder 21c (shown more clearly in FIG. 3,) which limits the extent to which the valve stem may enter the channel.

Figure 3A:
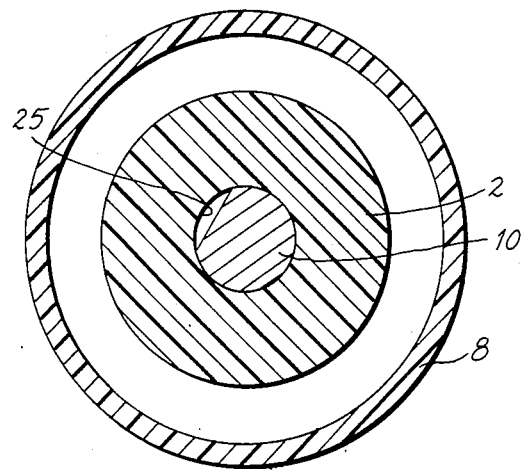
FIG. 3(a) is a cross-sectional view of the push-element taken along the arrow of FIG. 2
Figure 3B:
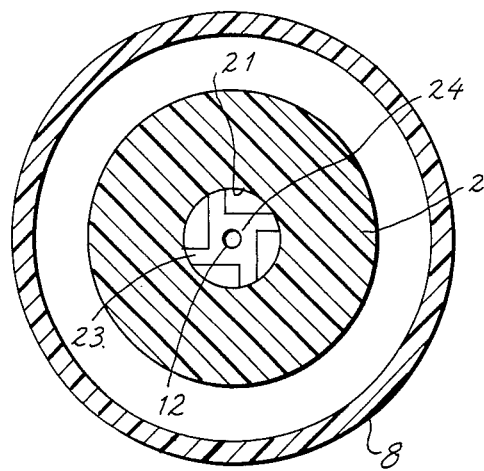
FIG. 3(b) is the same cross-sectional view with an obstructing piece removed.
Figure 4:
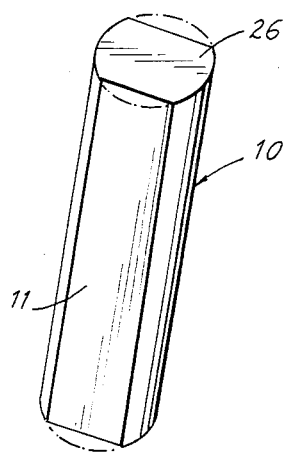
FIG. 4 is a perspective view the internal part of the push-element of FIG. 1.

The other end of the channel 21 is closed by a wall 21b, which has a spray opening 12 which has a smaller diameter than the channel. The wall 21b has a central portion and an outer portion, the outer portion being thicker than the central portion. As shown in FIG. 3, at least one groove 23 is formed on an inner surface of the wall 21b. These grooves extend from a cylindrical wall of the channel to a cavity 24 which surrounds the opening 12, so as to provide a spraying chamber. (At least one groove is required; however, a greater number, for example, four, may be used.) The grooves 23 are not radially arranged, but rather are sequentially circumferentially arranged to provide a swirling movement to liquid expelled through the opening 12, whereby a satisfactory spraying movement may be obtained.

The channel 21 is filled, along a major part of its length and a substantial portion of its cross-sectional area, with a rod 10 which is substantially cylindrically shaped but which has two flat parts 11. This rod limits the effective cross-sectional area through which liquid can flow, and also reduces the amount of dead space 14 in the channel. A bar having a square cross-section also may be used. As a result, there is at least one longitudinal passage 25 which carries the liquid up to the wall 21b, along grooves 23, and through the cavity 24 and opening 12, thereby providing an excellent spraying action.

It should be clear from the above description that the improvement embodied in the subject invention results from the formation of a nozzle as an integral part of the push-element 2, rather than as a separately-fitted piece. Because of this integral formation, there is no danger of the nozzle being ejected forcibly from the sprayer, and hence injected into a nostril or ear. Also, the formation of grooves in the wall 21b makes construction less expensive than the former practice of forming recesses or protrusions on an inner surface of the push-member.

The above-described construction allows the end of the external part 20 to be molded with rounded surfaces 15, 16, thereby avoiding the sharp, angular edges which normally are characteristic of an externally-mounted nozzle housing, and which may cause damage when the push-element is inserted. The greatly restricted dead space 14 limits product spillage and prevents the expelled from being contaminated when exposed under uncontrolled hygienic conditions.

It should be clearly understood that, while a preferred embodiment of the invention has been described, various changes and modifications may be made without departing from the spirit and scope of the invention.

What is claimed is:

1. An elongate push-element, for spraying a liquid, in combination with a container (1) for holding a liquid, said container having a valve stem (4), said push-element fitting over said valve stem (4), said push-element comprising:

a one-piece molded elongate external member (20) having a central channel (21) extending vertically axially within said external member, said central channel having one end (21a) which is open, said external member further including a wall (21b) integrally formed as a part of said external member and inseparable from said external member, wherein said wall substantially closes a second, opposite end of said central channel, said wall having an opening (12) extending therethrough to form an inner periphery of the wall which surrounds said opening, said opening having a diameter smaller than that of said central channel and through which liquid is expelled, said wall further having at least one groove (23) formed therein, said at least one groove extending non-radially outwardly from the opening, wherein a swirling motion is imported to the liquid as it is expelled; and an internal member (10) comprising a rod having a cross-section of smaller area than said central channel and larger area than said opening and having an end section (26) substantially perpendicular to a longitudinal axis of said rod, said internal member being separate from said external member, said container (1) and said valve stem (4) and inserted into said central channel through said one end, wherein at least a passage (25) is formed.

2. A push-element as recited in claim 1, wherein said wall has a central portion and an outer portion, said central portion having lesser thickness than said outer portion, said opening extending through said central portion, wherein a cavity (24) is formed around said opening.

3. A push-element as recited in claim 2, said at least one groove comprises at least four grooves extending substantially circumferentially and non-radially from said opening.

* * * * *

REEXAMINATION CERTIFICATE (2395th)
United States Patent [19]
Brunet et al.

[11] B1 4,801,093
[45] Certificate Issued  Sep. 20, 1994

[54] PUSH-NIPPLE FOR MEDICAL SPRAYER

[75] Inventors: Michel Brunet, Colombe la Commanderie; Firmin Garcia, Evreux, both of France

[73] Assignee: Establissements Valois, Le Neubourg, France

Reexamination Request:
No. 90/002,863, Oct. 23, 1992

Reexamination Certificate for:
Patent No.: 4,801,093
Issued: Jan. 31, 1989
Appl. No.: 623,867
Filed: Jun. 25, 1984

[30] Foreign Application Priority Data
Jun. 24, 1983 [FR] France ............................. 83 10450

[51] Int. Cl.$^5$ ............................................. B05B 1/34
[52] U.S. Cl. ............................ 239/490; 239/337; 239/493
[58] Field of Search ............... 239/490, 491, 492, 493, 239/494, 337; 222/321, 402.1, 402.13, 402.2

[56] References Cited

U.S. PATENT DOCUMENTS

| | | | |
|---|---|---|---|
| 2,775,483 | 12/1956 | Treharne, Jr. et al. | 222/402.25 |
| 2,974,880 | 3/1961 | Stewart et al. | 239/493 |
| 3,169,673 | 2/1965 | Focht | 222/402.13 X |
| 3,323,690 | 6/1967 | Monahon | 222/402.13 |
| 3,333,744 | 8/1967 | Nilsen et al. | 222/402.13 |
| 3,361,301 | 1/1968 | Meshberg | 222/402.13 X |
| 3,363,808 | 1/1968 | Gorman | 222/215 X |
| 3,379,381 | 4/1968 | Decaux | 239/493 X |
| 3,406,911 | 10/1968 | Keeney | 239/490 |
| 3,493,179 | 2/1970 | Lee | 239/493 X |
| 3,495,922 | 2/1970 | Steinmann | 222/402.1 X |
| 3,635,406 | 1/1972 | Scheindel | 239/490 |
| 3,652,018 | 3/1972 | Focht | 239/491 X |
| 4,143,822 | 3/1979 | Bennett | 239/490 |
| 4,273,290 | 6/1981 | Quinn | 239/493 |
| 4,367,847 | 1/1983 | Bayer | 239/490 X |
| 4,371,097 | 2/1983 | O'Neill | 222/383 X |

*Primary Examiner*—Kevin P. Shaver

[57] ABSTRACT

An elongate push-element (2) having a nozzle integrally formed with an external part (20) thereof, so that the nozzle cannot be forcibly ejected from a container which expels liquid under pressure. An opening (21a) at one end of an internal channel (21) may be slidably fitted on a valve stem (4) of a container (1), so that the push-element may be used with a variety of valve types.

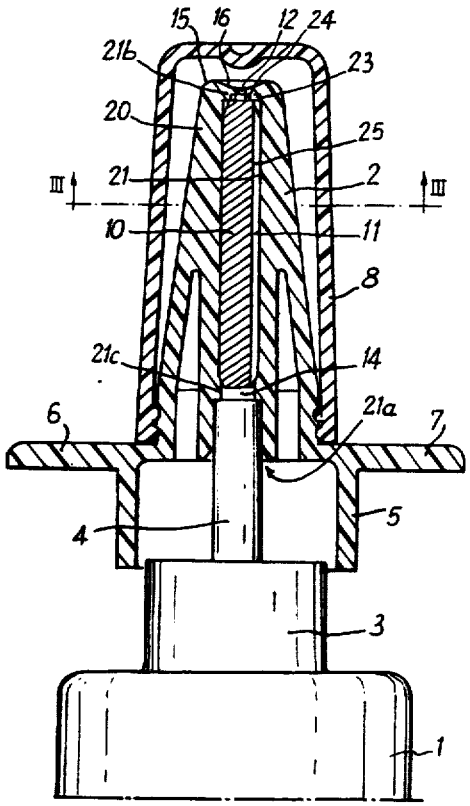

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2 and 3, dependent on an amended claim, are determined to be patentable.

New claims 4–10 are added and determined to be patentable.

1. An elongate push-element, for spraying a liquid, in combination with a container (1) for holding a liquid, said container having a valve stem (4), said push-element fitting over said valve stem (4), said push-element comprising:
   a one-piece molded elongate external member (20) having a central channel (21) extending vertically axially within said external member, said central channel having one end (21a) which is open, said external member further including a wall (21b) integrally formed as a part of said external member and inseparable from said external member, wherein said wall substantially closes a second, opposite end of said central channel, said wall having an opening (12) extending therethrough to form an inner periphery of the wall which surrounds said opening, said opening having a diameter smaller than that of said central channel and through which liquid is expelled, said wall further having at least one groove (23) formed therein, said at least one groove extending non-radially outwardly from the opening, wherein a swirling motion is [imported] *imparted* to the liquid as it is expelled; and
   an internal member (10) comprising a rod having a cross-section of smaller area than said central channel and larger area than said opening and having an end section (26) substantially perpendicular to a longitudinal axis of said rod, said internal member being separate from said external member, said container (1) and said valve stem (4) and inserted into said central channel through said one end, wherein at least a passage (25) is formed, *and wherein said elongate external member (20) has an internal shoulder (21c) near said open end (21a) for limiting the insertion of said valve stem (4) into said central channel, said rod being spaced apart from said valve step (4), thus defining a dead space (14) between said valve stem and said rod, and wherein said dead space communicates with said passage (25).*

*4. A push-element as recited in claim 1, wherein said elongate external member (20) further comprises a lower end portion, said lower end portion including a pair of elongated flanges (6, 7) extending therefrom and which are substantially perpendicular with respect to said central channel, said flanges providing a substantial finger gripping surface thereby to facilitate actuation of said push-element.*

*5. A push-element as recited in claim 4, further comprising a skirt (5) which extends below said flanges (6, 7) and conceals said valve stem (4).*

*6. A push-element as recited in claim 1, wherein said rod is substantially cylindrically shaped but has at least one flat part (11) which, together with said central channel, forms said passage (25), said rod thereby reducing an amount of dead volume in said central channel.*

*7. A push-element as recited in claim 1, wherein said elongate external member (20) is adapted to spray one of a medicine and a hygienic product in a body orifice.*

*8. A push-element as recited in claim 7, wherein said elongate external member (20) has an external surface, which gradually tapers from a position near said open end (21a) toward said opening (12), to facilitate insertion into the body orifice.*

*9. A push-element as recited in claim 1, wherein said rod has a uniform cross-section.*

*10. An elongate push-element, for spraying a liquid into a body orifice, in combination with a container (1) for holding a liquid, said container having a valve stem (4), said push-element fitting over said valve stem (4), said push-element comprising:*
   *a one-piece molded elongate external member (20) comprising a lower end portion and an upper end portion which is slim relative to said lower end portion and is operative to penetrate into the body orifice, said lower end portion including means (6, 7) for gripping said elongate external member (20), said external member having a central channel (21) extending vertically axially within said external member, said central channel having one end (21a) which is open, said external member further including a wall (21b) integrally formed as a part of said external member and inseparable from said external member, wherein said wall substantially closes a second, opposite end of said central channel, said wall having an opening (12) extending therethrough to form an inner periphery of the wall which surrounds said opening, said opening having a diameter smaller than that of said central channel and through which liquid is expelled, said wall further having at least one groove (23) formed therein, said at least one groove extending non-radially outwardly from the opening, wherein a swirling motion is imparted to the liquid as it is expelled; and*
   *an internal member (10) comprising a rod having a uniform cross-section of smaller area than said central channel and larger area than said opening and having an end section (26) substantially perpendicular to a longitudinal axis of said rod, said internal member being separate from said external member, said container (1) and said valve stem (4) and inserted into said central channel through said one end, wherein at least a passage (25) is formed.*

* * * * *